(12) United States Patent
Joseph

(10) Patent No.: US 11,517,578 B1
(45) Date of Patent: Dec. 6, 2022

(54) TOPICAL FORMULATIONS CONTAINING ERYTHRITOL AND METHODS OF TREATING SKIN CONDITIONS

(71) Applicant: InnoMed Technologies, Inc., Encino, CA (US)

(72) Inventor: John Joseph, Westlake Village, CA (US)

(73) Assignee: InnoMed Technologies, Inc., Encino, CA (US)

( * ) Notice: Subject to any disclaimer, the term of this patent is extended or adjusted under 35 U.S.C. 154(b) by 0 days.

(21) Appl. No.: 17/673,532

(22) Filed: Feb. 16, 2022

Related U.S. Application Data

(60) Provisional application No. 63/227,322, filed on Jul. 29, 2021.

(51) Int. Cl.
| | |
|---|---|
| *A61K 31/70* | (2006.01) |
| *A61K 33/30* | (2006.01) |
| *A61P 17/10* | (2006.01) |
| *A61K 9/00* | (2006.01) |
| *A61K 45/06* | (2006.01) |

(52) U.S. Cl.
CPC ............ *A61K 31/70* (2013.01); *A61K 9/0014* (2013.01); *A61K 33/30* (2013.01); *A61K 45/06* (2013.01); *A61P 17/10* (2018.01)

(58) Field of Classification Search
None
See application file for complete search history.

(56) References Cited

U.S. PATENT DOCUMENTS

| | | | | |
|---|---|---|---|---|
| 8,858,967 | B2 * | 10/2014 | Astruc | A61K 47/14 514/28 |
| 2007/0041924 | A1 * | 2/2007 | Gupta | A61Q 19/00 424/70.13 |
| 2007/0248651 | A1 * | 10/2007 | Sawits | A61K 31/525 514/474 |

FOREIGN PATENT DOCUMENTS

| | | | | | |
|---|---|---|---|---|---|
| CN | 1082406 | A | * | 2/1994 | ............. A61K 33/30 |
| CN | 106265264 | A | * | 1/2017 | ........... A61K 8/4913 |
| CN | 107334845 | A | * | 11/2017 | ......... A61K 31/4166 |
| CN | 109432385 | A | * | 3/2019 | ........... A61K 31/355 |
| CN | 110037217 | A | * | 7/2019 | ............... A23L 2/39 |
| CN | 112022783 | A | * | 12/2020 | ............. A61K 8/345 |
| JP | H11116436 | A | * | 4/1999 | ............. A61K 31/00 |

OTHER PUBLICATIONS

Anglenius, H., & Tiihonen, K. (2020). Evaluation of xylitol as an agent that controls the growth of skin microbes: *Staphylococcus aureus, Staphylococcus epidermidis*, and Cutibacterium acnes. The Microbiological Society of Korea, 56(1), 54-58. (Year: 2020).*

Kishishita, M., Ushijima, T., Ozaki, Y., & Ito, Y. (1979). Biotyping of Propionibacterium acnes isolated from normal human facial skin. Applied and Environmental Microbiology, 38(4), 585-589. (Year: 1979).*

Lim, Jong Hyun et al., Penetration of an antimicrobial zinc-sugar alcohol complex into *Streptococcus* mutans biofilms, Scientific Reports, Published Online: Nov. 1, 2018, (2018) 8:16154 | DOI:10.1038/s41598-018-34366-y, 8 pages.

* cited by examiner

*Primary Examiner* — Dale R Miller

(74) *Attorney, Agent, or Firm* — Entralta P.C.; James F. Fleming; Peter D. Weinstein

(57) ABSTRACT

Embodiments include formulations and methods for topical administration of sugar alcohol to treat a skin condition such as acne. A formulation can include a moisturizer, an emollient, a sugar alcohol and zinc. The sugar alcohol can be erythritol. The erythritol can be administered with zinc chloride. The erythritol and zinc chloride can be formulated at a molar ratio of about 3:1. The methods can also include administration of a therapeutic amount of a second agent such as benzoyl peroxide or a retinoid.

8 Claims, No Drawings

TOPICAL FORMULATIONS CONTAINING ERYTHRITOL AND METHODS OF TREATING SKIN CONDITIONS

RELATED APPLICATIONS

The present application claims priority to U.S. Provisional Application No. 63/227,322 filed Jul. 29, 2021, the contents of which are incorporated herein by reference.

FIELD OF THE INVENTION

The invention relates generally to topical administration of medicaments and more specifically, to methods of treating skin conditions such as acne using a sugar alcohol and zinc.

BACKGROUND

Acne, also known as acne vulgaris, is a long-term skin condition that occurs when dead skin cells and oil from the skin clog hair follicles. Signs and symptoms of acne include blackheads or whiteheads, pimples, oily skin and scarring in some patients. Acne mainly affects areas of the skin that have a high number of oil glands such as the face, upper part of the chest and back. Although generally considered a cosmetic concern, acne can lead to anxiety, reduced self-esteem and depression.

Acne commonly occurs in adolescence and affects an estimated 80-90% of teenagers in the Western world. Although acne becomes less common in adulthood, it persists in nearly half of affected people into their twenties and thirties, and a smaller group continues to have difficulties in their forties. Risk factors for the development of acne, other than genetics, have not been conclusively identified. Possible secondary contributors include hormones, infections, diet, and stress. The anaerobic bacterial species *Cutibacterium acnes* contributes to the development of acne, but its exact role is not well understood. There are specific substrains of *C. acnes* associated with normal skin and others with moderate or severe inflammatory acne. It is unclear whether these undesirable strains evolve on-site or are acquired, or possibly both depending on the person.

Many different treatments exist for acne. These include alpha hydroxy acid, anti-androgen medications, antibiotics, antiseborrheic medications, azelaic acid, benzoyl peroxide, hormonal treatments, steroids, keratolytic soaps, nicotinamide, retinoids and salicylic acid. Acne treatments work in at least four different ways including: reducing inflammation, hormonal manipulation, killing *C. acnes*, and normalizing skin cell shedding and sebum production in the pore to prevent blockage. Typical treatments include topical therapies such as antibiotics, benzoyl peroxide, and retinoids, and systemic therapies, including antibiotics, hormonal agents, and oral retinoids.

Antibiotics can be applied to the skin (i.e., dermal application) or taken orally. They work by killing *C. acnes* and reducing inflammation. Although multiple guidelines call for healthcare providers to reduce the rates of prescribed oral antibiotics, many providers do not follow this guidance. Oral antibiotics remain the most commonly prescribed systemic therapy for acne. Widespread broad-spectrum antibiotic overuse for acne has led to higher rates of antibiotic-resistant *C. acnes* strains worldwide, especially to the commonly used tetracycline (e.g., doxycycline) and macrolide antibiotics (e.g., topical erythromycin).

Commonly used antibiotics include clindamycin, erythromycin, metronidazole, sulfacetamide, and tetracyclines (e.g., doxycycline or minocycline). Antibiotics applied to the skin are typically used for mild to moderately severe acne. Oral antibiotics are generally more effective than topical antibiotics and produce faster resolution of inflammatory acne lesions than topical applications.

Antibiotic treatments for acne have shortcomings. Antibiotics, especially broad-spectrum antibiotics, can present side effects including nausea, indigestion, vomiting, diarrhea, bloating and stomach cramping. Oral antibiotics are not recommended for longer than three months. Longer durations of antibiotic treatment are associated with the development of antibiotic resistance. And while antibiotics reduce bacteria and inflammation, they do nothing to reduce pore blockages and the formation of microcomedones (the tiny beginnings of a pimple under the skin).

Accordingly, there is a need for more effective treatments of acne. Aspects of the present invention include topical formulations and methods that include erythritol and zinc for treating for acne.

SUMMARY OF THE INVENTION

Aspects of the present disclosure teach certain benefits in construction and use which give rise to the exemplary advantages described below.

One embodiment is a method of treating acne vulgaris (i.e., acne). The treatment can reduce the size and/or number of comedones, papules and/or pustules. The method includes topical administration of a therapeutic amount of a sugar alcohol and zinc. The sugar alcohol can be erythritol, xylitol, mannitol, sorbitol, ethylene glycol, glycerol, threitol, arabitol, xylitol, ribitol, mannitol, galactitol, fucitol, iditol, inositol, volemitol, isomalt, maltitol, lactitol, maltotriitol, maltotetraitol and/or polyglycitol.

In one embodiment, the sugar alcohol is erythritol and the erythritol and zinc are provided at a molar ratio of about 3:1.

The method can also include administration of another agent or medicament to treat acne such as benzoyl peroxide, a retinoid, a steroid, an antibiotic, azelaic acid, salicylic acid, dapsone, a contraceptive, an anti-androgen agent or isotretinoin to the subject.

In another embodiment, the sugar alcohol and zinc are co-administered with a transdermal penetrant. The formulation can also include a humectant, an emulsifier and/or an emollient.

In one embodiment, the method includes administration of one or more additional agents such as benzoyl peroxide, a retinoid, a steroid, an antibiotic, azelaic acid, salicylic acid, dapsone, a contraceptive, an anti-androgen agent and isotretinoin.

The topical formulation can have a pH of 9-11. Alternatively, it can have a pH of 7-10.5. In one embodiment, the topical formulation.

Another embodiment is a method of treating a skin condition. The method can include a step of administering a medicament to an area of skin of a subject. The medicament can include zinc chloride and erythritol. The zinc chloride and erythritol can be at a molar ratio of about 3:1. The skin condition can be acne, cellulitis, erysipelas, bacterial folliculitis, hot tub folliculitis, furuncles, carbuncles, impetigo, erythrasma and/or MRSA skin infection.

In one embodiment, multiple agents are administered together to treat a skin condition. The active agents can act synergistically with one another.

Other features and advantages of aspects of the present invention will become apparent from the following more detailed description, taken in conjunction with the accompanying drawings, which illustrate, by way of example, the principles of aspects of the invention.

Definitions

Reference in this specification to "one embodiment/aspect" or "an embodiment/aspect" means that a particular feature, structure, or characteristic described in connection with the embodiment/aspect is included in at least one embodiment/aspect of the disclosure. The use of the phrase "in one embodiment/aspect" or "in another embodiment/aspect" in various places in the specification are not necessarily all referring to the same embodiment/aspect, nor are separate or alternative embodiments/aspects mutually exclusive of other embodiments/aspects. Moreover, various features are described which may be exhibited by some embodiments/aspects and not by others. Similarly, various requirements are described which may be requirements for some embodiments/aspects but not other embodiments/aspects. Embodiment and aspect can in certain instances be used interchangeably.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. It will be appreciated that the same thing can be said in more than one way.

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

As applicable, the terms "about" or "generally", as used herein in the specification and appended claims, and unless otherwise indicated, means a margin of +/−20%. Also, as applicable, the term "substantially" as used herein in the specification and appended claims, unless otherwise indicated, means a margin of +/−10%. It is to be appreciated that not all uses of the above terms are quantifiable such that the referenced ranges can be applied.

The term "subject" or "patient" refers to any single animal, more preferably a mammal (including such non-human animals as, for example, dogs, cats, horses, rabbits, zoo animals, cows, pigs, sheep, and non-human primates) for which treatment is desired. Most preferably, the patient herein is a human.

The term "medicament," "active agent" or "active ingredient" refers to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed. An active agent can be a primary active agent, or in other words, the component(s) of a composition to which the whole or part of the effect of the composition is attributed. An active agent can be a secondary agent, or in other words, the component(s) of a composition to which an additional part and/or other effect of the composition is attributed.

In an embodiment, a "pharmaceutical composition" is intended to include the combination of an active agent with a carrier, inert or active, in a sterile composition suitable for diagnostic or therapeutic use in vitro, in vivo or ex vivo. In one aspect, the pharmaceutical composition is substantially free of endotoxins or is non-toxic to recipients at the dosage or concentration employed.

In an embodiment, as used herein, the terms "treating," "treatment" and the like are used herein to mean obtaining a desired pharmacologic and/or physiologic effect. The effect may be prophylactic in terms of completely or partially preventing a disorder or sign or symptom thereof, and/or may be therapeutic in terms of amelioration of the symptoms of the disease or infection, or a partial or complete cure for a disorder and/or adverse effect attributable to the disorder.

The term "bioavailability" refers to the fraction of an administered dose of unchanged drug that reaches the systemic circulation. For example, when a medication is administered intravenously, its bioavailability is 100%. However, when a medication is administered via other routes (such as orally), its bioavailability generally decreases due to incomplete absorption and first-pass metabolism. Bioavailability is one of the essential tools in pharmacokinetics, as bioavailability must be considered when calculating dosages for non-intravenous routes of administration.

The term "erythritol" refers to a four-carbon sugar alcohol that is often used as a food additive and sugar substitute. It is naturally occurring and can be made from corn using enzymes and fermentation. Its formula is $C_4H_{10}O_4$, or $HO(CH_2)(CHOH)_2(CH_2)OH$; specifically, one particular stereoisomer with that formula.

The term *Cutibacterium acnes* (formerly *Propionibacterium acnes*) is the relatively slow growing, typically aerotolerant anaerobic, gram-positive bacterium (rod) linked to the skin condition of acne. It can also cause chronic blepharitis and endophthalmitis, the latter particularly following intraocular surgery. Its genome has been sequenced and a study has shown several genes can generate enzymes for degrading skin and proteins that may be immunogenic (activating the immune system). The species is largely commensal and part of the skin flora present on most healthy adult humans' skin. It is usually barely detectable on the skin of healthy preadolescents. It lives, among other things, primarily on fatty acids in sebum secreted by sebaceous glands in the follicles. It may also be found throughout the gastrointestinal tract.

The term "microcomedone" refers to clinically non-visible central precursor lesions of acne that are induced by sebaceous hyperplasia as well as altered follicular growth and differentiation and evolve into both comedones and inflammatory lesions. Targeting microcomedone formation can be effective in the prevention and therapeutic control of acne. Every comedone and inflamed pimple begins its life as a microcomedone.

In an embodiment, "an effective amount" refers to the amount of the defined component sufficient to achieve the desired chemical composition or the desired therapeutic result. The desired result is the alleviation or amelioration of the signs, symptoms, or causes of a skin disease, or any other desired alteration of a biological system. For treating acne, the signs and symptoms can include the number of comedones, papules and/or pustules. When the desired result is a therapeutic response, the effective amount will, without limitation, vary depending upon the specific disease or symptom to be treated or alleviated, the age, gender and weight of the subject to be treated, the dosing regimen of the formulation, the severity of the disease condition, the manner of administration and the like, all of which can be determined readily by one of skill in the art. A desired effect may, without necessarily being therapeutic, also be a cosmetic effect, in particular for treatment for disorders of the skin described herein.

In an embodiment, as used herein, the terms "treating," "treatment" and the like are used herein, without limitation, to mean obtaining a desired pharmacologic and/or physiologic effect. The effect may be prophylactic in terms of completely or partially preventing a disorder or sign or symptom thereof, and/or may be therapeutic in terms of amelioration of the symptoms of the disease or infection, or a partial or complete cure for a disorder and/or adverse effect attributable to the disorder.

All numerical designations, e.g., pH, temperature, time, concentration, and molecular weight, including ranges, are to be understood as approximations in accordance with common practice in the art. When used herein, the term "about" may connote variation (+) or (−) 1%, 5% or 10% of the stated amount, as appropriate given the context. It is to be understood, although not always explicitly stated, that the reagents described herein are merely exemplary and that equivalents of such are known in the art.

Many known and useful compounds and the like can be found in Remington's Pharmaceutical Sciences (13th Ed), Mack Publishing Company, Easton, Pa. —a standard reference for various types of administration. As used herein, the term "formulation(s)" means a combination of at least one active ingredient with one or more other ingredient, also commonly referred to as excipients, which may be independently active or inactive. The term "formulation" may or may not refer to a pharmaceutically acceptable composition for administration to humans or animals and may include compositions that are useful intermediates for storage or research purposes.

As the patients and subjects of the invention method are, in addition to humans, veterinary subjects, formulations suitable for these subjects are also appropriate. Such subjects include livestock and pets as well as sports animals such as horses, greyhounds, and the like.

For purposes herein, a formulation, a formulation for topical delivery and a transdermal delivery formulation are each a formulation for transdermal delivery, including, the topical delivery of an active ingredient for the treatment of a syndrome and or a disease in an individual.

DETAILED DESCRIPTION

Embodiments include formulations and methods for treat a skin condition such as acne. Conventional methods of treating acne include topical antibiotics. Commonly used antibiotics, either applied to the skin or taken orally, include clindamycin, erythromycin, metronidazole, sulfacetamide, and tetracyclines. However, topical formulations are often ineffective in part because the active agents remain at the surface of the skin. Oral antibiotics are generally overprescribed and can lead to antibiotic-resistant $C.$ $acnes$ strains.

Small amounts of Zinc are essential for metabolic processes and have a positive impact on bone formation. It has been proposed that zinc ions act as an antimicrobial agent by deactivating proteins, causing structural changes in microbial membranes and affecting microbial nucleic acids, although the efficacy is insufficient to eradicate mature biofilms. Sugar alcohols such as xylitol also have antimicrobial effects. Xylitol is often used to control oral biofilms due to its safety and ability to inhibit the formation of biofilms. In particular, xylitol-containing chewing gums are widely used worldwide.

The combination of zinc chloride-erythritol can have an additive or synergistic effect in fighting bacteria. Zinc and sugar alcohols have demonstrated antimicrobial activity and can be used for removing biofilms.

Without wishing to be bound by theory, it is believed that the compounds described herein are effective treatments for acne due, at least in part, to the antimicrobial effect of the zinc chloride-erythritol mixture. Applicants propose that acne can be effectively treated by preventing or ameliorating bacterial growth at or near skin pores and hair follicles. The topical formulation allows the zinc chloride-erythritol mixture to effectively reach regions at or below the outer layer of skin (i.e., the epidermis). Accordingly, embodiments include formulations and methods for topical administration of erythritol and zinc.

In one embodiment, the erythritol and zinc are used at a molar ratio of about 3:1. Data suggests that this ratio is most effective against bacteria, including $Cutibacterium$ $acnes$ (i.e., $C.$ $acnes$). The erythritol and zinc can be combined in a topical lotion. The lotion can also have a humectant, an emulsifier and an emollient.

In another embodiment, the zinc and erythritol can be combined with one or more additional acne medications. For example, the formulation can be co-administered with benzoyl peroxide, a retinoid, a steroid, an antibiotic, azelaic acid, salicylic acid, dapsone, a contraceptive, an anti-androgen agent or isotretinoin to the subject. In one embodiment, the agent works synergistically with zinc and erythritol. In one embodiment, the second agent reduces inflammation. In another embodiment, the second agent is an exfoliant. For example, topical retinoids can work in conjunction with topical antibiotics. They can exfoliate the skin and reduce the formation of comedones (blocked pores).

Zinc chloride and erythritol can be used at a specific ratio. In one embodiment, a mixture of zinc chloride and erythritol has a molar ratio of about 1:3. In one embodiment, a mixture of zinc chloride and erythritol has a molar ratio of about 1:1.3. In one embodiment, a mixture of zinc chloride and erythritol has a molar ratio of about 1:1.5. In one embodiment, a mixture of zinc chloride and erythritol has a molar ratio of about 1:1.75. In one embodiment, a mixture of zinc chloride and erythritol has a molar ratio of about 1:2. In one embodiment, a mixture of zinc chloride and erythritol has a molar ratio of about 1:4. In one embodiment, a mixture of zinc chloride and erythritol has a molar ratio of about 1:5. In one embodiment, a mixture of zinc chloride and erythritol has a molar ratio of about 1:6. In one embodiment, zinc chloride and erythritol are used in equimolar amounts.

Topical Formulation Components

Embodiments include a lotion or cream for administration of medicaments to a subject. It is placed on the skin to deliver a specific dose of an agent through the skin. The agent can be delivered across the skin into a localized subdermal location (e.g., near areas with acne). For example, a lotion can inhibit growth of c. *acnes* and reduce inflammation. The lotion or cream can be applied directly to the affected area such as the face. In am embodiment, a topical formulation is applied to the skin and the mucous membranes of the eye (an eye ointment), chest, vulva, anus, and nose.

In an embodiment, a topical formulation can be in the form of any of the following. A solution which in an embodiment can be one or more of a water or alcoholic lotion containing a dissolved active ingredient(s).

In another embodiment, a topical formulation can be a lotion, which is generally thicker than a solution, and in some embodiments, it can comprise an oil as well as water or an alcohol. In an embodiment, a lotion can separate into two or more different parts with time such that the lotion may need to be shaken into suspension before use.

In a further embodiment, a topical formulation can be a cream. A cream can in an embodiment, be thicker than a lotion. One result is that a cream is capable of maintaining its shape. In an embodiment, a lotion is comprised of a 50/50 emulsion of oil and water. A cream may also require a preservative to extend its shelf life.

In an embodiment, a topical formulation can be a foam.

In another embodiment, a topical formulation can be in the form of an ointment. In an embodiment, an ointment is comprised of a composition that in an embodiment is a semi-solid, water-free or nearly water-free (80% oil). An ointment can be greasy, sticky, emollient, protective and/or occlusive. An ointment can be homogeneous, viscous, semi-solid preparation, which in some embodiments are greasy, a thick oil (oil 80%-water 20%) with a high viscosity; that is intended for external application to the skin or mucous membranes. Ointments do not always require the addition of a preservative, so ointments are less likely to result in a contact allergy. An ointment is generally comprised of one or more of a hydrocarbon (paraffin), wool fat, beeswax, macrogols, emulsifying wax, cetrimide and/or a vegetable oil (olive oil, arachis oil, coconut oil).

In another embodiment, a topical formulation can be a gel. In an embodiment, a gel is comprised of an aqueous and/or alcoholic monophasic semisolid emulsion and/or a cellulose. A gel can, in an embodiment, liquefy upon contact with skin. Gels often includes preservatives and fragrances. In an embodiment, a gel can comprise a cellulose cut with alcohol or acetone.

In a further embodiment, a topical formulation can be a paste. In an embodiment, a paste is comprised of a concentrated suspension of oil, water and/or powder.

In an embodiment, a topical formulation can be an aerosol, foam or spray. Generally, an aerosol, foam or spray is comprised of a solution with a pressurized propellant. In a further embodiment, a topical formulation is a powder.

A powder can comprise, for example, a talc (a mineral) or a starch (corn starch, corn cob powder or other vegetable starch). A powder can be inhaled, for example, for a nasal surgery.

In an embodiment, a topical formulation is a solid. A solid can comprise an antiperspirant or a sunscreen stick, which may melt on reaching body temperature (eg, a suppository).

In a further embodiment, a topical formulation is a tincture. In an embodiment, a tincture comprises a high percentage of alcohol.

In an embodiment, a topical formulation comprises a vesicle within which the active agent, e.g., erythritol and zinc, are encapsulated and then released at a later time. The release can occur following application to the site on the skin or the release can occur over a period of time to ensure. The vesicle can comprise a liposome or a nanoparticle. The nanoparticle can include a lipid-based nanoparticles, niosomes, transfersomes, ethosomes, dendrimers, micellar nanoparticles, polymeric as well as metallic and magnetic nanostructures. A nanoparticle can be of any size, but preferably less than 100 nm, less than 95 nm, less than 90 nm, less than 85 nm, less than 80 nm, less than 75 nm, less than 70 nm, less than 65 nm, less than 60 nm, less than 55 nm, less than 50 nm, less than 45 nm, less than 40 nm, less than 35 nm, less than 30 nm, less than 25 nm, less than 20 nm, less than 15 nm, less than 10 nm, or less than 5 nm in diameter.

In an embodiment, a topical formulation is administered using a pressure-driven jet. The threshold velocity for penetration into human skin in an embodiment is 100-200 m/s. In another embodiment, the threshold velocity is at least 100 m/s, at least 110 m/s, at least 120 m/s, at least 130 m/s, at least 140 m/s, at least 150 m/s, at least 160 m/s, at least 170 m/s, at least 180 m/s, at least 190 m/s, at least 200 m/s. In another embodiment, the threshold velocity is no more than 100 m/s, no more than 110 m/s, no more than 120 m/s, no more than 130 m/s, no more than 140 m/s, no more than 150 m/s, no more than 160 m/s, no more than 170 m/s, no more than 180 m/s, no more than 190 m/s, no more than 200 m/s In another embodiment, a topical or transdermal formulation is comprised of a transdermal patch. An advantage of a transdermal patch is that it provides precise dosing of an active (a sugar alcohol and/or zinc). A transdermal patch can include an adhesive to allow for fixation of the patch on the body of a patient. It can also include a liner that protects the patch during storage. For transdermal patch that includes a liner, the liner can be removed prior to use. A transdermal patch can also include the active ingredient, including, but limited to a drug in solution in direct contact with liner and becoming exposed upon removal of the liner. The active ingredient can also be contained in a reservoir. The active ingredient can be part of a formulation that comprises a permeation enhancer to promote the increase in the delivery of the drug transdermally. The transdermal patch can also include an adhesive that serves to adhere the components of the patch together along with adhering the patch to the skin. A transdermal patch can also include a membrane that in an embodiment, is capable of controlling the release of the drug from the reservoir and/or different layer of the patch. A transdermal patch can also include a backing that protects the patch from the outer environment. A transdermal patch can also include a matrix filler that provides bulk to the matrix and/or a stiffening agent. A transdermal patch can also include other components, including a stabilizer (e.g., an anti-oxidant) or a preservative. A transdermal patch can include a single-layer or a multi-layer active agent (e.g., drug)-in-adhesive. A transdermal patch can also include a vapor patch that serves to adhere the various layers together but also to release a vapor. The vapor can be comprised of an essential oil.

In an embodiment, a topical formulation is administered through the use of a sponge as a carrier for a liquid medicine.

In another embodiment, a topical formulation is administered through a tape. In an embodiment, a tape can be a cordran tape.

In an embodiment, a transdermal formulation is administered through the Stratum Corneum layer via tiny microchannels created by a medical micro-needling device, which are known in the arts, including variants. In a further embodiment, delivery is through the use of iontophoresis. In another embodiment, a thermal based approach can be used to enhance transdermal penetration of an active agent, including a drug, and further including erythritol and/or zinc. A thermal based approach can include the use of heat.

In one embodiment, a topical formulation comprises an aluminum acetate topical solution. An aluminum acetate topical solution is generally colorless, with a faint acetous odor and sweetish taste. It is applied topically as an astringent after dilution with 10-40 parts of water. An aluminum acetate topical formulation is used in many types of dermatologic creams, lotions, and pastes. An aluminum acetate topical formulation can be premeasured and packed as tablets and powders.

An advantage of a transdermal drug delivery route over other types of delivery is that the formulation can provide a controlled release of the agent. Further, transdermal administration is not affected by stomach or digestive issues. Oral consumption of erythritol and zinc would not be expected to significantly help treat acne, even in high doses. Further, people can benefit from drugs that are absorbed slowly and regularly. With a transdermal formulation, a medicament can be released in small quantities over a long period of time.

Other advantages are related to dosing. Large doses of agents can cause dose-dependent toxicity in many cases. For example, oral administration of vitamin A can result in hypervitaminosis A. The main problems associated with the vitamin A are its half-life, fast absorption (due to lipophilicity) and its toxicity (due to high loading and frequent dosing). Also, some drugs undergo first-pass metabolism, which prevents their delivery to the desired site of action. Furthermore, many hydrophilic or lipophilic drugs show either poor dissolution or poor absorption on oral administration. With a transdermal formulation, the effective concentration of an agent can be applied at the desired site without painful delivery.

Acne Vulgaris

Acne, also known as acne vulgaris can be caused by bacteria, specifically the proliferation of *Cutibacterium acnes*, or *C. acnes*. Topical antibiotics (e.g., clindamycin and erythromycin) are common treatments. Oral antibiotics are used to treat acne also but have shortcomings as described above.

*C. acnes* is an ordinary resident of the skin, but in those with acne the population grows out of control. These bacteria irritate the skin's follicles, creating inflamed papules and pustules. Applying a topical antibiotic can reduce the amount of bacteria to help control acne. Topical antibiotics can also reduce inflammation, so they can be most effective with inflamed breakouts rather than non-inflamed blemishes or blackheads.

In an embodiment, a sugar alcohol is administered topically or transdermally to a subject. Although erythritol is described in the examples, other sugar alcohols can be used. Sugar alcohols include erythritol, xylitol, mannitol, sorbitol, ethylene glycol, glycerol, threitol, arabitol, xylitol, ribitol, mannitol, galactitol, fucitol, iditol, inositol, volemitol, isomalt, maltitol, lactitol, maltotriitol, maltotetraitol and polyglycitol. In an embodiment, a combination of sugar alcohols is administered to a subject to treat acne.

Another embodiment is directed to a method of treating acne, the method comprising i) selecting a therapeutic agent (e.g. a sugar alcohol and/or zinc) described herein and formulating the therapeutic agent in a topical formulation, and iii) administering the formulation topically and/or transdermally in an amount effective to inhibit or prevent the growth and proliferation of *C. acnes*.

Another embodiment is directed to a method of preventing acne comprising administering topically and/or transdermally an effective amount of a formulation that includes a sugar alcohol such as erythritol and zinc. Formulations provided herein are also used in methods of treating other skin conditions that result from bacteria growth such as cellulitis, erysipelas, bacterial folliculitis, hot tub folliculitis, furuncles, carbuncles, impetigo, erythrasma or MRSA skin infection.

In another aspect, formulations of the invention can be administered or co-administered with one or more additional agents that target acne. For example, the topical formulation can be co-administered with benzoyl peroxide, a retinoid, a steroid, an antibiotic, azelaic acid, salicylic acid, dapsone, a contraceptive, an anti-androgen agent or isotretinoin to the subject.

Although the examples describe the use of the zinc chloride-erythritol mixture to treat acne, the formulations can be used to treat other ailments, including skin infections. For example, cellulitis, erysipelas, bacterial folliculitis, hot tub folliculitis, furuncles, carbuncles, impetigo, erythrasma and MRSA skin infection can be treated using the formulations described herein.

Embodiments include a topical lotion or cream for administration of a agent (e.g., erythritol) to a subject. It is placed on the skin to deliver a specific dose of an agent through the skin. The agent can be delivered across the skin into a localized subdermal location. In one embodiment, the lotion or cream includes one or more of a fragrance, a sunscreen, hyaluronic acid, an alpha-hydroxy acid (e.g., glycolic acid and lactic acid), a ceramide, retinol, argan oil, vitamin C, vitamin E, vitamin B3, green tea and algae extract.

An advantage of a transdermal drug delivery route over other types of delivery is that the formulation can provide a controlled release of the agent. Conventional transdermal delivery systems are generally ineffective for use with agents and medications that are large molecules and/or hydrophilic molecules.

There are other advantages to transdermal administration of medicaments. Small molecules can be inactivated or degraded by the stomach or liver. Transdermal administration is not affected by stomach or digestive issues. Further, people can benefit from drugs that are absorbed slowly and regularly. With a transdermal formulation, a medicament can be released in small quantities over a long period of time.

Other advantages are related to dosing. Large doses of agents can cause dose-dependent toxicity in many cases. For example, oral administration of vitamin A can result in hypervitaminosis A. The main problems associated with the vitamin A are its half-life, fast absorption (due to lipophilicity) and its toxicity (due to high loading and frequent dosing). Also, some drugs undergo first-pass metabolism, which prevents their delivery to the desired site of action. Furthermore, many hydrophilic or lipophilic drugs show either poor dissolution or poor absorption on oral administration. With a topical or transdermal formulation, the effective concentration of an agent can be applied at the desired site without painful delivery.

In an embodiment, a topical formulation comprises the components of Table 1:

TABLE 1

General Active Agent Formulation

| Ingredient | Weight (%) |
|---|---|
| Emollient/moisturizer | 10-20% |
| Alcohol | 0.5-2% |
| Oil | 1-5% |
| Surfactant | 0.5-2% |
| Deionized Water | 50-80% |
| Active Agent | 1-5% |
| Total | 100.00% |

In another embodiment, a topical formulation comprises the components of Table 2 and the active agent (i.e., zinc chloride and erythritol) is 5% w/w:

TABLE 2

"A" Formulation-5% active agent

| Ingredient | Weight (%) |
|---|---|
| A Humectant | 10% |
| Deionized Water | 83% |
| Poloxamer 407 | 2% |
| Zinc Chloride | 1.25% |
| Erythritol | 3.75% |
| Total | 100.00% |

In another embodiment, a topical formulation comprises the components of Table 3 and the active agent (i.e., zinc chloride and erythritol) is 10% w/w:

TABLE 3

"B" Formulation-10% active agent

| Ingredient | Weight (%) |
|---|---|
| A Humectant | 10% |
| Deionized Water | 75% |
| Poloxamer 407 | 2% |
| Zinc Chloride | 2.5% |
| Erythritol | 7.5% |
| Total | 100.00% |

In another embodiment, a topical formulation comprises the components of Table 3 and the active agent (i.e., zinc chloride and erythritol) is 20% w/w:

TABLE 3

"B" Formulation-20% active agent

| Ingredient | Weight (%) |
|---|---|
| A Humectant | 10% |
| Deionized Water | 65% |
| Poloxamer 407 | 2% |
| Zinc Chloride | 5% |
| Erythritol | 15% |
| Total | 100.00% |

In an aspect, the concentration of active agent is about 1%, about 1.5%, about 2%, about 7.5%, about 12.5%, about 15%, about 17.5%, about 20%, about 25% or about 30%. In an aspect, the concentration of active agent is at least 0.5%, at least 1%, at least 1.5%, at least 2%, at least 7.5%, at least 12.5%, at least 15%, at least 17.5%, at least 20%, at least 25% or at least 30%. In an aspect, the concentration of active agent is not more than 0.5%, not more than 1%, not more than 1.5%, not more than 2%, not more than 7.5%, not more than 12.5%, not more than 15%, not more than 17.5%, not more than 20%, not more than 25% or not more than 30%.

In an embodiment, the concentration of deionized water in a transdermal formulation is at least 0.1%, at least 0.2%, at least 0.3%, at least 0.4%, at least 0.5%, at least 0.6%, at least 0.7%, at least 0.8%, at least 0.9%, at least 1%, at least 2%, at least 3%, at least 4%, at least 5% or more. In an embodiment, the concentration of Deionized Water in a transdermal formulation is about 0.1%, about 0.2%, about 0.3%, about 0.4%, about 0.5%, about 0.6%, about 0.7%, about 0.8%, about 0.9%, about 1%, about 2%, about 3%, about 4%, about 5% or more. In an embodiment, the concentration of deionized water in a transdermal formulation is from 0.1% to 5%, from 0.2% to 4%, from 0.3% to 3%, 0.4%-2%, 0.5% to 1%, from 0.6% t 0.9%, from 0.7% to 0.8%, from 0.4% to 1.5%, from 0.3% to 0.7% or from 0.4% to 0.6%. In an embodiment, the concentration of deionized water in a formulation is no more than 0.1%, no more than 0.2%, no more than 0.3%, no more than 0.4%, no more than 0.5%, no more than 0.6%, no more than 0.7%, no more than 0.8%, no more than 0.9%, no more than 1%, no more than 2%, no more than 3%, no more than 4%, no more than 5% or more.

In an aspect, the formulation also includes safflower oil in an amount of at least 1%, at least 5%, at least 7.5%, at least 10%, at least 11%, at least 11.06%, at least 12%, at least 13%, at least 14%, at least 15%, at least 16%, at least 17%, at least 18%, at least 19%, at least 20% or more. In an aspect, the concentration of Safflower oil in a formulation is about 1%, about 5%, about 7.5%, about 10%, about 11%, about 11.06%, about 12%, about 13%, about 14%, about 15%, about 16%, about 17%, about 18%, about 19%, about 20% or more. In an aspect, the concentration of Safflower oil in a topical formulation is from 1% to 20%, from 5% to 19%, from 7.5% to 18%, from 10% to 17%, from 11% to 16%, from 11.06%, 12% from 11% to 12%, from 12% to 14%, from 13% to 14%, from 10% to 12%, from 10.5% to 12.5% or from 11% to 11.25%. In an aspect, the concentration of safflower oil in a topical formulation is no more than 1%, no more than 5%, no more than 7.5%, no more than 10%, no more than 11%, no more than 11.06%, no more than 12%, no more than 13%, no more than 14%, no more than 15%, no more than 16%, no more than 17%, no more than 18%, no more than 19%, no more than 20%.

In a further aspect, the topical formulation includes oleic acid. The concentration of oleic acid can be, for example, at least 1%, at least 2%, at least 3%, at least 3.65%, at least 4%, at least 5%, at least 6%, at least 7%, at least 8%, at least 9%, at least 10% or more. In a further aspect, the concentration of oleic acid in a topical formulation is about 1%, about 2%, about 3%, about 3.65%, about 4%, about 5%, about 6%, about 7%, about 8%, about 9%, about 10% or more. In a further aspect, the concentration of oleic acid in a topical formulation is no more than 1%, no more than 2%, no more than 3%, no more than 3.65%, no more than 4%, no more than 5%, no more than 6%, no more than 7%, no more than 8%, no more than 9%, no more than 10% or more. In another aspect, the concentration of oleic acid in a transdermal formulation is from 1% to 10%, from 2% to 9%, from 2% to 3%, from 3% to 4%, from 3% to 8%, from 4% to 7%, from 5% to 6%, from 2 to 2.5% or from 2.5% to 4%.

In an aspect, the concentration of poloxamer 407 in a topical formulation is at least 10%, at least 15%, at least 20%, at least 25%, at least 28.75%, at least 30%, at least 35%, at least 40% or more. In an aspect, the concentration of poloxamer 407 in a topical formulation is not more than 10%, not more than 15%, not more than 20%, not more than 25%, not more than 28.75%, not more than 30%, not more than 35%, not more than 40% or more. In an aspect, the concentration of poloxamer 407 in a topical formulation is about 10%, about 15%, about 20%, about 25%, at least 28.75%, about 30%, about 35%, about 40% or more. In an aspect, the concentration of poloxamer 407 in a topical formulation is from 10% to 40%, is from 15% to 35%, is from 20% to 30%, is from 25% to 30%, is from 28% to 29%.

In another aspect, the formulation includes glucose. The concentration of glucose in a topical formulation can be, for example, at least 1%, at least 2%, at least 2.5%, at least 3%, at least 4%, at least 5%, at least 6%, at least 7%, at least 8%, at least 9% or more. In another aspect, the concentration of glucose in a topical formulation is about 1%, about 2%, about 2.5%, about 3%, about 4%, about 5%, about 6%, about 7%, about 8%, about 9% or more. In another aspect, the concentration of glucose in a topical formulation is no more than 1%, no more than 2%, no more than 2.5%, no more than 3%, no more than 4%, no more than 5%, no more than 6%, no more than 7%, no more than 8%, no more than 9% or more. In another aspect, the concentration of glucose in a topical formulation is from 1% to 10%, is from 2% to 9%, is from 2.5% to 5%, is from 2% to 3%, is from 3% to 8%, if from 4% to 7%, if from 5% to 6%, is from 2% to 4%, is from 1.5% to 3.5.

The formulation can also include penetrants including either or both chemical penetrants (CPEs) and peptide-based cellular penetrating agents (CPPs) that encourage transmission across the dermis and/or across membranes including cell membranes, as would be the case in particular for administration by suppository or intranasal administration, but for transdermal administration as well. In some embodiments, suitable penetrants include those that are described in the above-referenced US2009/0053290 ('290), WO2014/209910 ('910), and WO2017/127834. In addition to transdermal delivery formulations with penetrants, transdermal delivery can be affected by mechanically disrupting the surface of the skin to encourage penetration, or simply by supplying the formulation applied to the skin under an occlusive patch.

The formulation can also include a gelling component. Suitable gelling components also include isopropyl palmitate, ethyl laurate, ethyl myristate and isopropyl myristate. The gelling agent can be less than 5% w/w of the formulation. In some embodiments, the formulation includes a mixture of xanthan gum, sclerotium gum, pullulan, or a combination thereof in an amount less than 2% w/w, 5% w/w, or 10% w/w of the formulation. In some embodiments, the formulation includes Siligel™ in an amount between about 1-5% w/w or 5-15% w/w, or an equivalent mixture of xanthan gum, sclerotium gum, and pullulan. In some embodiments, the formulation includes a mixture of caprylic triglycerides and capric triglycerides in amount less than 2% w/w, 8% w/w, or 10% w/w of the formulation. In some embodiments, the formulation includes Myritol® 312 in an amount between about 0.5-10% w/w, or an equivalent mixture of caprylic triglycerides and capric triglycerides.

An additional component in the formulation can be an alcohol. The weight percentage of benzyl or other related alcohol in the final composition can be 0.5-20% w/w, and again, intervening percentages such as 1% w/w, 2% w/w, 3% w/w, 4% w/w, 5% w/w, 6% w/w, 7% w/w, 8% w/w, 9% w/w, or 10% w/w, and other intermediate weight percentages are included. Due to the aromatic group present in a topical formulation such as benzyl alcohol, the molecule has a polar end (the alcohol end) and a non-polar end (the benzene end). This enables the agent to dissolve a wider variety of topical formulation components.

In some embodiments, the formulation includes a detergent portion in an amount between about 1-70% w/w or 1-60% w/w. In some embodiments, the nonionic detergent provides suitable handling properties whereby the formulations are gel-like or creams at room temperature. Suitable nonionic detergents include poloxamers such as the nonionic surfactant Pluronic® and any other surfactant characterized by a combination of hydrophilic and hydrophobic moieties. Poloxamers are triblock copolymers of a central hydrophobic chain of polyoxypropylene flanked by two hydrophilic chains of polyethyleneoxide. Other nonionic surfactants include long chain alcohols and copolymers of hydrophilic and hydrophobic monomers where blocks of hydrophilic and hydrophobic portions are used.

In some embodiments, a topical formulation also contains surfactant, typically, nonionic surfactant at 2-25% w/w of a topical formulation along with a polar solvent wherein the polar solvent is present in an amount at least in molar excess of the nonionic surfactant. In these embodiments, typically, the composition comprises the above-referenced amounts of a topical formulation and benzyl alcohol along with a sufficient amount of a polar solution, typically an aqueous solution or polyethylene glycol solution that itself contains 10%-40% of surfactant, typically nonionic surfactant to bring the composition to 100%.

In some embodiments other additives are included such as a gelling agent, a dispersing agent and a preservative. An example of a suitable gelling agent is hydroxypropylcellulose, which is generally available in grades from viscosities of from about 5 cps to about 25,000 cps such as about 1500 cps. All viscosity measurements are assumed to be made at room temperature unless otherwise stated. The concentration of hydroxypropylcellulose may range from about 1 w/w to about 2% w/w of the composition. Other gelling agents are known in the art and can be used in place of, or in addition to hydroxypropylcellulose. An example of a suitable dispersing agent is glycerin. Glycerin is typically included at a concentration from about 5% w/w to about 25% w/w of the composition. A preservative may be included at a concentration effective to inhibit microbial growth, ultraviolet light and/or oxygen-induced breakdown of composition components, and the like. When a preservative is included, it may range in concentration from about 0.01% w/w to about 1.5% w/w of the composition.

Additional components that can also be included in a topical formulation are fatty acids, terpenes, lipids, and cationic, and anionic detergents. In some embodiments, a topical formulation further comprises tranexamic acid in an amount less than 2% w/w, 5% w/w, or 10% w/w of the formulation. In some embodiments, a topical formulation further comprises a polar solvent in an amount less than 2% w/w, 5% w/w, 10% w/w, or 20% w/w of the transdermal delivery formulation. In some embodiments, a topical formulation further comprises a humectant, an emulsifier, an emollient, or a combination thereof. In some embodiments, a topical formulation further comprises almond oil in an amount less than about 5% w/w. In some embodiments, a formulation further comprises a mixture of thermoplastic polyurethane and polycarbonate in an amount less than about 5% w/w. In some embodiments, a topical formulation further comprises phosphatidylethanolamine in an amount less than about 5% w/w. In some embodiments, a topical formulation further comprises an inositol phosphatide in an amount less than about 5% w/w.

Other solvents and related compounds that can be used in some embodiments include acetamide and derivatives, acetone, n-alkanes (chain length between 7 and 16), alkanols, diols, short chain fatty acids, cyclohexyl-1,1-dimethylethanol, dimethyl acetamide, dimethyl formamide, ethanol, ethanol/d-limonene combination, 2-ethyl-1,3-hexanediol, ethoxydiglycol (Transcutol® by Gattefosse, Lyon, France), glycerol, glycols, lauryl chloride, limonene N-methylformamide, 2-phenylethanol, 3-phenyl-1-propanol, 3-phenyl-2-propen-1-ol, polyethylene glycol, polyoxyethylene sorbitan monoesters, polypropylene glycol 425, primary alcohols (tridecanol), 1,2-propane diol, butanediol, $C_3$-$C_6$ triols or their mixtures and a polar lipid compound selected from $C_{16}$ or $C_{18}$ monounsaturated alcohol, $C_{16}$ or $C_{18}$ branched saturated alcohol and their mixtures, propylene glycol, sorbitan monolaurate sold as Span® 20 by Sigma-Aldrich, squalene, triacetin, trichloroethanol, trifluoroethanol, trimethylene glycol and xylene.

Fatty alcohols, fatty acids, fatty esters, are bilayer fluidizers that can be used in some embodiments. Examples of suitable fatty alcohols include aliphatic alcohols, decanol, lauryl alcohol (dodecanol), unolenyl alcohol, nerolidol, 1-nonanol, n-octanol, and oleyl alcohol. Examples of suitable fatty acid esters include butyl acetate, cetyl lactate, decyl N, N-dimethylamino acetate, decyl N, N-dimethylamino isopropionate, diethyleneglycol oleate, diethyl sebacate, diethyl succinate, diisopropyl sebacate, dodecyl N,N-dimethyamino acetate, dodecyl (N, N-dimethylamino)-butyrate, dodecyl N, N-dimethylamino isopropionate, dodecyl 2-(dimethyamino) propionate, E0-5-oleyl ether, ethyl acetate, ethylaceto acetate, ethyl propionate, glycerol monoethers, glycerol monolaurate, glycerol monooleate, glycerol monolinoleate, isopropyl isostearate, isopropyl linoleate, isopropyl myristate, isopropyl myristate/fatty acid monoglyceride combination, isopropyl palmitate, methyl acetate, methyl caprate, methyl laurate, methyl propionate, methyl valerate, 1-monocaproyl glycerol, monoglycerides (medium chain length), nicotinic esters (benzyl), octyl acetate, octyl N,N-dimethylamino acetate, oleyl oleate, n-pentyl N-acetylprolinate, propylene glycol monolaurate, sorbitan dilaurate, sorbitan dioleate, sorbitan monolaurate, sorbitan monooleate, sorbitan trilaurate, sorbitan trioleate, sucrose coconut fatty ester mixtures, sucrose monolaurate, sucrose monooleate, tetradecyl N,N-dimethylamino acetate. Examples of suitable fatty acid include alkanoic acids, caprid acid, diacid, ethyloctadecanoic acid, hexanoic acid, lactic acid, lauric acid, linoelaidic acid, linoleic acid, linolenic acid, neodecanoic acid, oleic acid, palmitic acid, pelargonic acid, propionic acid, and vaccenic acid. Examples of suitable fatty alcohol ethers include a-monoglyceryl ether, E0-2-oleyl ether, E0-5-oleyl ether, E0-10-oleyl ether, ether derivatives of polyglycerols and alcohols, and (1-O-dodecyl-3-O-methyl-2-O-(2',3'-dihydroxypropyl glycerol).

Examples of completing agents that can be used in some embodiments include β- and γ-cyclodextrin complexes, hydroxypropyl methylcellulose (e.g., Carbopol® 934), patchs, naphthalene diamide diimide, and naphthalene diester diimide.

One or more antioxidants can be included, such as vitamin C, vitamin E, proanthocyanidin and a-lipoic acid typically in concentrations of 0.1% — 2.5% w/w.

In some applications, it is desirable to adjust the pH of a topical formulation to assist in permeation or to adjust the nature of the target compounds in the subject. In some instances, the pH is adjusted to a level of pH 9-11 or 10-11 which can be done by providing appropriate buffers or simply adjusting the pH with base.

A topical formulation can include other components that act as excipients or serve purposes other than for treatment of acne. For example, preservatives like antioxidants e.g., ascorbic acid or α-lipoic acid and anti-inflammatory agents may be included. Other components apart from therapeutically active ingredients and components that are the primary effectors of dermal penetration may include those provided for aesthetic purposes such as menthol or other aromatics, and components that affect the physical state of the composition such as emulsifiers, for example, Durosoft®. Typically, these ingredients are present in very small percentages of the compositions. It is understood that these latter ancillary agents are neither therapeutically ingredients nor are they components that are primarily responsible for penetration of the skin. The components that primarily effect skin penetration have been detailed as described above. However, some of these substances have some capability for effecting skin penetration. See, for example, Kunta, J. R. et al, *J. Pharm. Sci.* (1997) 86:1369-1373, describing penetration properties of menthol.

The application method is determined by the nature of the treatment but may be less critical than the nature of the formulation itself. If the application is to a skin area, it may be helpful in some instances to prepare the skin by cleansing or exfoliation. In some instances, it is helpful to adjust the pH of the skin area prior to application of a topical formulation itself. The application of a topical formulation may be by simple massaging onto the skin or by use of devices such as syringes or pumps. Patches could also be used. In some cases, it is helpful to cover the area of application to prevent evaporation or loss of a transdermal delivery formulation.

Where the application area is essentially skin, it is helpful to seal-off the area of application subsequent to supplying a topical formulation and allowing the penetration to occur so as to restore the skin barrier. A convenient way to do this is to apply a composition comprising linoleic acid which effectively closes the entrance pathways that were provided by the penetrants of the invention. This application, too, is done by straightforward smearing onto the skin area or can be applied more precisely in measured amounts.

In addition to the compositions and formulations of the invention per se, the methods can employ a subsequent treatment with linoleic acid. As transdermal treatments generally open up the skin barrier, which is, indeed, their purpose, it is useful to seal the area of application after the treatment is finished. Thus, treatment with a topical formulation may be followed by treating the skin area with a composition comprising linoleic acid to seal off the area of application. The application of linoleic acid is applicable to any transdermal procedure that results in impairing the ability of the skin to act as a protective layer. Indeed, most transdermal treatments have this effect as their function is to allow the active component to pass through the epidermis to the dermis at least, and, if systemic administration is achieved, through the dermis itself.

Additional therapeutic agents can be included in the compositions. For example, hydrocortisone or hydrocortisone acetate may be included in an amount ranging from 0.25% w/w to about 0.5% w/w. Menthol, phenol, and terpenoids, e.g., camphor, can be incorporated for cooling pain relief. For example, menthol can be included in an amount ranging from about 0.1% w/w to about 1.0% w/w.

In some applications a formulation for transdermal delivery may, for example, comprise: Aveeno®, for example in an amount between about 10-95% w/w; between about 20-85% w/w, between about 20-75% w/w, between about 20-50% w/w.

The formulation described in this specification may also comprise more than one therapeutic compound as desired for the particular indication being treated, preferably those with complementary activities that do not adversely affect the other proteins. A topical formulation to be used for in vivo administration can be sterile. This can be accomplished, for instance, without limitation, by filtration through sterile filtration membranes, prior to, or following, preparation of a topical formulation or other methods known in the art, including without limitation, pasteurization.

Packaging and instruments for administration may be determined by a variety of considerations, such as, without limitation, the volume of material to be administered, the conditions for storage, whether skilled healthcare practitioners will administer or patient self-compliance, the dosage regime, the geopolitical environment (e.g., exposure to extreme conditions of temperature for developing nations), and other practical considerations.

In certain embodiments, kits can comprise, without limitation, one or more cream or lotion comprising one or more formulations described herein. In various embodiments, the kit can comprise formulation components for transdermal, topical, or subcutaneous administration, formulated to be administered as an emulsion coated patch. In all of these embodiments and others, the kits can contain one or more lotion, cream, patch, or the like in accordance with any of the foregoing, wherein each patch contains a single unit dose for administration to a subject.

Imaging components can optionally be included, and the packaging also can include written or web-accessible instructions for using a transdermal delivery formulation. A container can include, for example, a vial, bottle, patch, syringe, pre-filled syringe, tube or any of a variety of formats well known in the art for multi-dispenser packaging.

In some embodiments, a suitable topical formulation comprises: Siligel™ in an amount less than about 5% w/w; water in an amount between about 10-65% w/w; isopropyl palmitate in an amount between about 0.5-10% w/w; stearic Acid in an amount between about 0.25-10% w/w; cetyl alcohol in an amount between about 0.25-10% w/w; glycerin in an amount between about 0.25-5% w/w; a topical formulation in an amount between about 0.25-10% w/w; ethanol in an amount less than about 5% w/w; benzyl alcohol in an amount less than about 5% w/w; sodium hydroxide 50% w/v in an amount between about 0.1-5% w/w; and sodium bicarbonate in an amount between about 1-32% w/w.

In some embodiments, a suitable topical formulation comprises Aveeno® in an amount between about 20-85% w/w; and sodium bicarbonate (3DF) in an amount between about 15-45% w/w.

In some embodiments, a topical formulation comprises Aveeno® in an amount between about 20-85% w/w; and sodium bicarbonate in an amount between about 15-45% w/w.

The surprising effects achieved by the formulations and methods of the present invention are in part attributable to an improved topical formulation that enhances delivery of a carbonate salt through the skin. The present formulations can include a nonionic surfactant. Applicant has found that by employing carbonate salts with particle sizes as disclosed herein, delivered with the penetrants as disclosed herein, and in some embodiments providing a combination of a nonionic surfactant and a polar gelling agent, the penetration capabilities of the carbonate salts of the resulting formulation and the effective level of delivery of the carbonate salts has been enhanced.

A topical formulation of the disclosure may be prepared in a number of ways. Typically, the components of a topical formulation are simply mixed together in the required amounts. Alternatively, some subset of these components can first be mixed and then "topped off" with the remaining components either simultaneously or sequentially. The precise manner of preparing a topical formulation will depend on the choice of carbonates and the percentages of the remaining components that are desirable with respect to that carbonate salt. In some embodiments, the water is in an amount between about 10-85% w/w, 15-50% w/w, or 15-45% w/w of the formulation.

The topical formulation is a multi-component mixture, whereby the particular concentrations of the penetration enhancers are informed in part by the molecular mass of the sodium bicarbonate, or sodium bicarbonate and the therapeutic agent to be transported. A topical formulation enables therapeutic agent to become bio-available to the target site within minutes of topical administration. A topical formulation permit the use of minimal concentrations of therapeutic agents, as little as $\frac{1}{1000}$th of concentrations required of alternative processes, while enabling bioactivity and positive clinical outcomes simultaneously. In some embodiments, the topical formulation comprises an alcohol in an amount less than 5% w/w of the formulation.

Administration and Dosing

A topical formulation provided herein can be topically administered in any form. For administration for the treatment of skin conditions a sufficient amount of the topical composition can be applied onto a desired area and surrounding skin, for example, in an amount sufficient to cover a desired skin surface. A topical formulation can be applied to any skin surface, including for example, facial skin, and the skin of the hands, neck, chest and/or scalp.

In applying a topical formulation of the invention, a topical formulation itself is simply placed on the skin and spread across the surface and/or massaged to aid in penetration. The amount of topical formulation used is typically sufficient to cover a desired surface area. In some embodiments, a protective cover is placed over the formulation once it is applied and left in place for a suitable amount of time, i.e., 5 minutes, 10 minutes, 20 minutes or more; in some embodiments an hour or two. The protective cover can simply be a bandage including a bandage supplied with a cover that is impermeable to moisture. This essentially locks in the contact of a topical formulation to the skin and prevents distortion of a topical formulation by evaporation in some cases. The composition may be applied to the skin using standard procedures for application such as a brush, a syringe, a gauze pad, a dropper, or any convenient applicator. More complex application methods, including the use of delivery devices, may also be used, but are not required. In an alternative to administering topically to intact skin, the surface of the skin may also be disrupted mechanically by the use of spring systems, laser powered systems, systems propelled by Lorentz force or by gas or shock waves including ultrasound and may employ microdermabrasion such as by the use of sandpaper or its equivalent or using microneedles or electroporation devices. Simple solutions of the agent(s) as well as the above-listed formulations that penetrate intact skin may be applied using occlusive patches, such as those in the form micro-patches. External reservoirs of the formulations for extended administration may also be employed.

In an alternative to administering topically to intact skin, the surface of the skin may also be disrupted mechanically by the use of spring systems, laser powered systems, use of iontophoresis, systems propelled by Lorentz force or by gas or shock waves including ultrasound and may employ microdermabrasion such as by the use of sandpaper or its equivalent or using microneedles or electroporation devices. Simple solutions of the agent(s) as well as the above-listed transdermal delivery formulations that penetrate intact skin may be applied using occlusive patches, such as those in the form of micro-patches. External reservoirs of the formulations for extended administration may also be employed.

Accordingly, in certain embodiments alternative methods of administering one or more therapeutic compounds or agents (e.g. medicaments) through intact skin are provided. As nonlimiting examples, these alternative methods might be selected from the following lists: on basis of working mechanism, spring systems, laser powered, energy-propelled, Lorentz force, gas/air propelled, shock wave (including ultrasound), on basis of type of load, liquid, powder, projectile, on basis of drug delivery mechanism, nano-patches, sandpaper (microdermabrasion), iontophoresis enabled, microneedles, on basis of site of delivery, intradermal, intramuscular, and subcutaneous injection. Other suitable delivery mechanisms include, without limitation, microneedle drug delivery, such as 3M Systems, Glide SDI (pushes drug as opposed to "firing" drug), MIT low pressure injectors, micropatches (single use particle insertion device), microelectro mechanical systems (MEMS), dermoelectroporation devices (DEP), transderm ionto system (DEP), TTS transdermal therapeutic systems, membrane-moderated systems (drug reservoir totally encapsulated in a shallow compartment), adhesive diffusion-controlled system (drug reservoir in a compartment fabricated from drug-impermeable metallic plastic backing), matrix dispersion type system (drug reservoir formed by homogeneously dispersing drug solids in a hydrophilic or lipophilic polymer matrix molder into medicated disc), and microreservoir system (combination of reservoir and matrix dispersion-type drug delivery system).

The application method is determined by the nature of the treatment but may be less critical than the nature of a topical formulation itself. If the application is to a skin area, it may be helpful in some instances to prepare the skin by cleansing or exfoliation. In some instances, it is helpful to adjust the pH of the skin area prior to application of the formulation itself. The application of a topical formulation may be by simple massaging onto the skin or by use of devices such as syringes or pumps. Patches could also be used. In some cases, it is helpful to cover the area of application to prevent evaporation or loss of the formulation.

Where the application area is essentially skin, it is helpful to seal-off the area of application subsequent to supplying a topical formulation and allowing the penetration to occur so as to restore the skin barrier. A convenient way to do this is to apply a composition comprising linoleic acid which effectively closes the entrance pathways that were provided by the penetrants of the invention. This application, too, is done by straightforward smearing onto the skin area or can be applied more precisely in measured amounts.

A topical formulation can be applied in a single, one-time application, once a week, once a bi-week, once a month, or from one to twelve times daily, for a period of time sufficient to alleviate a condition, disease, disorder, symptoms, for example, for a period of time of one week, from 1 to 12 weeks or more, from 1 to 6 weeks, from 2 to 12 weeks, from 2 to 8 weeks, from 2 to 6 weeks, from 2 to 4 weeks, from 4 to 12 weeks, from 4 to 8 weeks, or from 4 to 6 weeks. The present compositions can be administered, for example, at a frequency of once per day to hourly if needed. The presently described formulations can be topically administered once or more per day for a period of time from 1 week to 4 weeks, of from 1 week to 2 weeks, for 1 week, for 2 weeks, for 3 weeks, or for 4 weeks or more. In some instances, it may also be desirable to continue treatment indefinitely, for example, to inhibit recurring inflammation. A suitable administration for a topical formulation comprising a skin cream, lotion or ointment, for example is once, twice, three, four times daily, or hourly if needed.

As described above, if desired, other therapeutic agents can be employed in conjunction with those provided in the above-described compositions. The amount of active ingredients that may be combined with the carrier materials to produce a single dosage form will vary depending upon the host treated, the nature of the disease, disorder, or condition, and the nature of the active ingredients.

It is understood that a specific dose level for any particular patient will vary depending upon a variety of factors, including the activity of the specific active agent; the age, body weight, general health, sex and diet of the patient; the time of administration; the rate of excretion; possible drug combinations; the severity of the particular condition being treated; the area to be treated and the form of administration. One of ordinary skill in the art would appreciate the variability of such factors and would be able to establish specific dose levels using no more than routine experimentation.

Pharmacokinetic parameters such as bioavailability, absorption rate constant, apparent volume of distribution, unbound fraction, total clearance, fraction excreted unchanged, first-pass metabolism, elimination rate constant, half-life, and mean residence time can be determined by methods well known in the art.

A topical formulation in accordance with the subject matter described herein may be a topical dosage form packaged in, for example, a multi-use or single-use package, including for example, a tube, a bottle, a pump, a container or bottle, a vial, a jar, a packet, or a blister package.

Single dosage kits and packages containing a once per day amount of the topical formulation may be prepared. Single dose, unit dose, and once-daily disposable containers of the topical formulation are also provided.

The present topical formulation remains stable in storage for periods including up to about 5 years, between about 3 months and about 5 years, between about 3 months and about 4 years, between about 3 months and about 3 years, and alternately any time period between about 6 months and about 3 years.

A topical formulation described herein remains stable for up to at least 3 years at a temperature of less than or equal to 40° C. In an embodiment, the presently described topical formulation remains stable for at least 2 years at a temperature of less than or equal to 40° C. In an embodiment, the presently described topical formulation remains stable for at least 3 years at a temperature of less than or equal to 40° C. and at a humidity of up to 75% RH, for at least 2 years at a temperature of less than or equal to 40° C. and at a humidity of up to 75% RH, or for at least 3 years at a temperature of less than or equal to 30° C. and at a humidity of up to 75% RH. In a further embodiment, the presently described topical formulation in accordance with the subject matter described herein remains stable for an extended period of time when packaged in a multi-use container such as a bottle dispenser or the like, and exhibits equal to or even greater stability when packaged in a single-use package.

It is understood that a specific dose level for any particular patient will vary depending upon a variety of factors, including the activity of the specific active agent; the age, body weight, general health, sex and diet of the patient; the time of administration; the rate of excretion; possible drug combinations; the severity of the particular condition being treated; the area to be treated and the form of administration. One of ordinary skill in the art would appreciate the variability of such factors and would be able to establish specific dose levels using no more than routine experimentation.

Pharmacokinetic parameters such as bioavailability, absorption rate constant, apparent volume of distribution, unbound fraction, total clearance, fraction excreted unchanged, first-pass metabolism, elimination rate constant, half-life, and mean residence time can be determined by methods well known in the art.

A topical formulation in accordance with the subject matter described herein may be a topical dosage form packaged in, for example, a multi-use or single-use package, including for example, a tube, a bottle, a pump, a container or bottle, a vial, a jar, a packet, or a blister package.

Single dosage kits and packages containing a once per day amount of the topical formulation may be prepared. Single dose, unit dose, and once-daily disposable containers of the topical formulation are also provided.

Aspects of the present specification disclose that the symptoms associated with a disease or disorder (i.e., the presence of acne) described herein are reduced following application of a topical formulation by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% and the severity associated with a disease or disorder described herein is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. Aspects of the present specification disclose the symptoms associated with disease or disorder (i.e., the presence of acne) are reduced following application of a topical formulation by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

Aspects of the present specification disclose that the symptoms (i.e., the presence of acne) described herein are reduced following administration of a topical formulation of the present invention by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% and the presence of acne is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. Aspects of the present specification disclose the symptoms (i.e., the presence of acne) are reduced by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

Dosing can be single dosage or cumulative (serial dosing), and can be readily determined by one skilled in the art. A topical formulation of the present invention may be administered once, twice, three, four, five, six, seven, eight, nine, ten, eleven, twelve, thirteen, fourteen, fifteen, sixteen, seventeen, eighteen, nineteen, twenty or more times to a subject. For instance, treatment of a disease may comprise a one-time administration of an effective dose of a topical formulation as disclosed herein. Alternatively, treatment of a disease may comprise multiple administrations of an effective dose of a topical formulation as carried out over a range of time periods, such as, e.g., once daily, twice daily, thrice daily, once every few days, or once weekly. The timing of administration can vary from individual to individual, depending upon such factors as the severity of an individual's symptoms. For example, an effective dose of a topical formulation as disclosed herein can be administered to an individual once daily for an indefinite period of time, or until the individual no longer requires therapy. A person of ordinary skill in the art will recognize that the condition of the individual can be monitored throughout the course of treatment and that the effective amount of a topical formulation disclosed herein that is administered can be adjusted accordingly. In one embodiment, a topical formulation as disclosed herein is capable of decreasing the time to resolve the symptoms of a disease, including in an individual suffering from a disease by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% as compared to a patient not receiving the same treatment.

In a further embodiment, a topical formulation and its derivatives have half-lives of 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 1 week, 2 weeks, 3 weeks, 4 weeks, one month, two months, three months, four months or more.

In an embodiment, the period of administration of a topical formulation is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

In aspects of this embodiment, a therapeutically effective amount of a topical formulation disclosed herein reduces or alleviates symptoms (e.g., the presence of acne) in an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a topical formulation disclosed herein reduces or alleviates the presence of acne in an individual by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a topical formulation disclosed herein reduces or alleviates the presence of acne in an individual by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 70%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

A topical formulation disclosed herein can include a therapeutically effective amount of one or more agents. As used herein, the term "effective amount" is synonymous with "therapeutically effective amount", "effective dose", or "therapeutically effective dose" and when used in reference to reducing or alleviate symptoms of acne in an individual refers to the minimum dose of a therapeutic disclosed herein necessary to achieve the desired therapeutic effect and includes a dose sufficient to reduce or alleviates symptoms of acne in an individual. The effectiveness of a topical formulation disclosed herein capable of reducing or alleviating symptoms can be determined by observing an improvement in an individual based upon one or more clinical symptoms, such as a reduction in the number of comedones, papules and/or pustules. Maintenance or a reduction of symptoms of an ailment can also be subjective to a patient. The effectiveness of a topical formulation disclosed herein in an individual can be determined by observing an improvement the skin complexion. The effectiveness of the topical formulation disclosed herein is also capable of enhancing the quality of life of an individual as compared to the same individual if the topical formulation is not administered.

The appropriate effective amount of a topical formulation disclosed herein to be administered to an individual can be determined by a person of ordinary skill in the art by taking into account factors, including, without limitation, an improvement in the individual based upon one or more clinical symptoms, and/or physiological indicators associated with improvements skin complexion, reduced number of comedones, papules and/or pustules, the particular characteristics, history and risk factors of the patient, such as, e.g., age, weight, general health and the like, or any combination thereof. Additionally, where repeated administration of a topical formulation is used, an effective amount of a topical formulation will further depend upon factors, including, without limitation, the frequency of administration, the half-life of the transdermal delivery formulation, or any combination thereof. It is known by a person of ordinary skill in the art that an effective amount of a topical formulation disclosed herein can be extrapolated from in vitro assays and in vivo administration studies using animal models prior to administration to humans or animals.

Wide variations in the necessary effective amount are to be expected in view of the differing efficiencies of the various routes of administration. For instance, oral administration of a topical formulation disclosed herein generally would be expected to require higher dosage levels than administration by inhalation. Similarly, systemic administration of a topical formulation disclosed herein would be expected to require higher dosage levels than a local administration. Variations in these dosage levels can be adjusted using standard empirical routines of optimization, which are well-known to a person of ordinary skill in the art. The precise therapeutically effective dosage levels and patterns are preferably determined by the attending physician in consideration of the above-identified factors. One skilled in the art will recognize that the condition of the individual can be monitored throughout the course of therapy and that the effective amount of a therapeutic disclosed herein that is administered can be adjusted accordingly.

Aspects of the present specification disclose, in part, a reduction or alleviation of symptoms of acne such as comedones, papules and/or blemishes. As used herein, the term "treating," refers to reduction of the presence of acne. For example, the term "treating" can mean reduction of acne in an individual by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. The actual symptoms associated with acne are well known and can be determined by a person of ordinary skill in the art by using commonly known testing means and observations. Those of skill in the art will know the appropriate symptoms or indicators associated with acne and will know how to determine if an individual is a candidate for treatment as disclosed herein.

In an embodiment, a first topical formulation is administered to an individual and at a later date, a second topical formulation is administered to the same individual. In an embodiment, a first topical formulation is administered to an individual at the same time as a second topical formulation is administered to the individual.

In some embodiments, the glucose in an amount between about 0.05-10% w/w of the transdermal delivery formulation.

In some embodiments, the glucose is anhydrous dextrose in an amount between about 0.05-10% w/w of the transdermal delivery formulation.

In some embodiments, the formulation has a pH of 9-11.

In some embodiments, the formulation has a pH of 7-10.5.

In one embodiment, a topical formulation disclosed herein is capable of reducing the signs/symptoms associated with acne in an individual suffering from the acne by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% as compared to a patient not receiving the same treatment. In other aspects of this embodiment, an anti-acne topical formulation is capable of reducing the number of comedones or microcomedones in an individual suffering from a acne by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70% as compared to a patient not receiving the same treatment.

In a further embodiment, a topical formulation and its derivatives have half-lives of 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 1 week, 2 weeks, 3 weeks, 4 weeks, one month, two months, three months, four months or more.

In an embodiment, the period of administration of a topical formulation is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

In aspects of this embodiment, a therapeutically effective amount of a topical formulation disclosed herein reduces or maintains signs/symptoms associated with an ailment (i.e., acne) in an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a topical formulation disclosed herein reduces or maintains signs/symptoms associated with an ailment by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a topical formulation disclosed herein reduces or maintains signs/symptoms associated with an ailment by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

EXAMPLES

The following non-limiting examples are provided for illustrative purposes only in order to facilitate a more complete understanding of representative embodiments now contemplated. These examples are intended to be a mere subset of all possible contexts in which the components of the formulation may be combined. Thus, these examples should not be construed to limit any of the embodiments described in the present specification, including those pertaining to the type and amounts of components of the formulation and/or methods and uses thereof.

Example 1

Erythritol and Zinc to Treat Acne

In this example, a 18-year-old male visits a healthcare professional and complains of facial acne that has been persistent for the past three years. He describes sporadic facial breakouts that began gradually, varied in severity and never completely cleared. He explains that the breakouts contribute to feelings of low self-esteem. He tried over-the-counter (OTC) 5% benzoyl peroxide (BP) gels and washes, as well as multiple facial cleansing products, without improvement. A physical examination revealed a healthy teenager with 15 open and closed comedones, 10 papules, and 5 pustules on each half of the face and involving the forehead, cheeks and chin.

The healthcare professional administers the formulation of erythritol and zinc to the patient. As detailed in Table 2, the formulation includes erythritol (3.75%) and zinc chloride (1.25%). The formulation allows for effective transdermal administration of the zinc chloride-erythritol mixture which can prevent or ameliorate bacterial growth at or near skin pores and hair follicles.

The patient is also advised to continue daily use of an OTC facial wash. After washing and rinsing the face, the patient applies the formulation to the entire face. After five to ten minutes, the face can be rinsed with water. The routine is repeated each day (i.e., twice per day). Within ten days, the acne is resolved by about 80% (i.e., about 80% of the acne is gone). The comedones, papules and pustules are less apparent and only visible at close proximity. The patient resumes twice daily use of the formulation. Within two weeks the signs/symptoms of acne are resolved by about 95%. The patient has a clear complexion.

The patient is also advised to continue daily OTC facial washes and apply the transdermal formulation twice per week. The frequency can be increased if the patient observes a return of acne and/or a possible break out.

Transdermal administration allows direct absorption into a specific area. For example, a lotion can be applied to specific areas that are prone to acne. In this example, the patient applies the lotion to the forehead, cheeks and chin.

The lotion can include a topical formulation and the zinc chloride-erythritol mixture (collectively referred to as the formulation). In this example, the dose of the active agent (i.e. zinc chloride-erythritol mixture) is 5% w/w of the solution. A transdermal medicament presents several benefits. The lack of interference with food and alcohol is one advantage. Topical delivery avoids the GI tract and can increase bioavailability. Increased bioavailability permits lower doses which reduce the risk of side effects. Topical administration also allows for the patient to increase the volume and incidence of application based on need/symptoms.

Example 2

Erythritol and Zinc with Exfoliator

In this example, a 16-year-old female visits a healthcare professional and complains of facial acne that become gradually worse over the past two years. She describes monthly and sporadic facial breakouts that never completely clear. She tried OTC benzoyl peroxide (BP) gels and washes, as well as multiple facial cleansing products, with minimal or no significant improvement.

The healthcare professional administers the transdermal formulation of erythritol and zinc to the patient. As detailed in Table 2, the formulation includes erythritol (3.75%) and zinc chloride (1.25%). The formulation allows for effective transdermal administration of the zinc chloride-erythritol mixture which can prevent or ameliorate bacterial growth at or near skin pores and hair follicles.

The patient is also advised to wash her face daily. After washing and rinsing the face, the patient applies the formulation to the entire face. After five to ten minutes, the face can be rinsed with water. This routine is repeated each day (i.e., twice per day). Within ten days, the acne is resolved by about 65% (i.e., about 65% of the acne is gone).

The healthcare professional administers a retinoid to be used in conjunction with the formulation. The retinoid cream can help unclog pores and increase absorption of the zinc chloride-erythritol mixture. Specifically, a pea-sized amount of retinoid cream is applied over the skin once a day 20 to 30 minutes after washing the face. Thereafter, the patient applies the formulation in a similar manner. Within two weeks the signs/symptoms of acne are resolved by about 95%. The patient has a clear complexion.

The patient is also advised to continue daily regular use of facial washes and to apply the retinoid and transdermal formulation twice per week. The frequency can be increased if the patient observes a return of acne and/or a possible break out.

Example 3

Erythritol and Zinc with Steroid

In this example, a 17-year-old female visits a healthcare professional and complains of facial acne that become gradually worse over the past three to five years. She describes monthly and sporadic facial breakouts that never completely clear. She tried OTC benzoyl peroxide (BP) gels and washes, as well as multiple facial cleansing products, with minimal or no significant improvement.

The healthcare professional administers the formulation of erythritol and zinc to the patient. As detailed in Table 2, the formulation includes erythritol (3.75%) and zinc chloride (1.25%). The formulation allows for effective administration of the zinc chloride-erythritol mixture.

The patient is also advised to wash her face daily. After washing and rinsing the face, the patient applies the formulation to the entire face. After five to ten minutes, the face can be rinsed with water. This routine is repeated each day (i.e., twice per day). Within ten days, the acne is resolved by about 65% (i.e., about 65% of the acne is gone). The healthcare professional observes mild inflammation in around the cheeks and forehead.

The healthcare professional administers hydrocortisone to be used in conjunction with the formulation. Topical hydrocortisone can reduce the inflammation of acne, and the swollen appearance that comes with it. Specifically, hydrocortisone cream is applied over the skin once a day 20 to 30 minutes after washing the face. Thereafter, the patient applies the formulation in a similar manner. Within two weeks the signs/symptoms of acne are resolved by about 95%. The patient has a clear complexion.

The patient is also advised to continue daily regular use of facial washes and to apply the hydrocortisone and transdermal formulation twice per week. The frequency can be increased if the patient observes a return of acne and/or a possible break out.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method of ameliorating acne in a subject, the method comprising administration of a therapeutic amount of erythritol and zinc to the subject, wherein the erythritol and zinc are at a molar ration of about 3:1.

2. The method of claim 1, wherein the therapeutic amount of erythritol and zinc is administered topically to the subject.

3. The method of claim 1, further comprising administration of a therapeutic amount of benzoyl peroxide, a retinoid, a steroid, an antibiotic, azelaic acid, salicylic acid, dapsone, a contraceptive, an anti-androgen agent or isotretinoin to the subject.

4. A method of inhibiting growth of *Cutibacterium acnes* in a subject, the method comprising administration of a therapeutic amount of a formulation to the subject, wherein the formulation comprises:
   a) a moisturizer (1-5% w/w);
   b) an emollient (1-5% w/w);
   c) erythritol (about 3.75% w/w);
   d) zinc chloride (about 1.25% w/w); and
   e) water.

5. The method of claim 4, wherein the formulation is administered topically to the subject.

6. The method of claim 4, further comprising administration of one or more medicaments to the subject.

7. The method of claim 6, wherein the one or more medicaments is comprised of benzoyl peroxide, a retinoid, a steroid, an antibiotic, azelaic acid, salicylic acid, dapsone, a contraceptive, an anti-androgen agent and isotretinoin.

8. The method of claim 4, wherein the formulation further comprises one or more of a fragrance, a humectant and an emulsifier.

\* \* \* \* \*